US010837892B2

(12) United States Patent
Chinavare et al.

(10) Patent No.: US 10,837,892 B2
(45) Date of Patent: Nov. 17, 2020

(54) APPARATUS FOR TESTING A PROSTHESIS

(71) Applicant: TA Instruments—Waters L.L.C., Milford, MA (US)

(72) Inventors: Jason L. Chinavare, Minnetonka, MN (US); Sunoj Narayanan, Eden Prairie, MN (US); David L. Dingmann, St. Paul, MN (US); Lito Cruz Mejia, Savage, MN (US)

(73) Assignee: TA INSTRUMENTS WATERS LLC, Milford, MA (US)

( * ) Notice: Subject to any disclaimer, the term of this patent is extended or adjusted under 35 U.S.C. 154(b) by 681 days.

(21) Appl. No.: 15/160,615

(22) Filed: May 20, 2016

(65) Prior Publication Data

US 2016/0341651 A1 Nov. 24, 2016

Related U.S. Application Data

(60) Provisional application No. 62/164,929, filed on May 21, 2015.

(51) Int. Cl.
*G01N 15/06* (2006.01)
*A61F 2/82* (2013.01)
(Continued)

(52) U.S. Cl.
CPC ........... *G01N 15/0618* (2013.01); *A61F 2/82* (2013.01); *G01N 3/08* (2013.01);
(Continued)

(58) Field of Classification Search
USPC ....................................................... 73/61.72
See application file for complete search history.

(56) References Cited

U.S. PATENT DOCUMENTS 5,670,708 A * 9/1997 Vilendrer .............. G01M 99/00
73/37
7,591,198 B2 * 9/2009 Weldon .................... A61B 5/06
73/865.9
(Continued)

OTHER PUBLICATIONS

Conti, et al.; A Comprehensive Protocol and Procedural Considerations Designed to Evaluate the Shedding of Particles from Drug Eluting Stents, Presented at the Materials and Processes for Medical Devices Conference, Palm Desert, California (2007).*

*Primary Examiner* — Nimeshkumar D Patel
*Assistant Examiner* — Jean F Morello
(74) *Attorney, Agent, or Firm* — Womble Bond Dickinson (US) LLP; Deborah M. Vernon; Heath T. Misley

(57) ABSTRACT

Systems, methods, and devices are provided for testing a drug eluting prosthesis. A drug eluting prosthesis is placed within a conduit that is coupled at one end to a first conduit frame and at a second end to a second conduit frame. The first conduit frame is coupled to the second conduit frame using a movable shaft, such that the first conduit frame and the second conduit frame can move relative to each other. When the first conduit frame and the second conduit frame are moved relative to each other, they expose the conduit and the drug eluting prosthesis to compressive or tensile forces. While the drug eluting prosthesis is being exposed to compressive or tensile forces, a fluid flow is provided through the conduit to test the particle shed rate of the drug eluting prosthesis.

8 Claims, 8 Drawing Sheets

(51) Int. Cl.
*G01N 3/08* (2006.01)
*G01N 15/10* (2006.01)
*G01N 15/14* (2006.01)

(52) U.S. Cl.
CPC .. *A61F 2250/0067* (2013.01); *G01N 15/1459* (2013.01); *G01N 2015/0687* (2013.01); *G01N 2015/1062* (2013.01); *G01N 2015/1486* (2013.01); *G01N 2203/0242* (2013.01)

(56) References Cited

U.S. PATENT DOCUMENTS

| | | | |
|---|---|---|---|
| 8,196,478 B2 * | 6/2012 | Lorenz | A61F 2/82 73/818 |
| 2003/0110830 A1 * | 6/2003 | Dehdashtian | A61F 2/07 73/37 |
| 2007/0185534 A1 * | 8/2007 | Conti | G01N 3/56 607/1 |
| 2010/0225478 A1 * | 9/2010 | McCloskey | G01N 3/32 340/540 |
| 2011/0146385 A1 * | 6/2011 | Weinberg | G01N 3/36 73/37 |
| 2016/0003723 A1 * | 1/2016 | Chapman | G01N 3/26 73/37 |

* cited by examiner

APPARATUS FOR TESTING A PROSTHESIS

RELATED APPLICATIONS

This application claims priority to U.S. Provisional Patent Application Ser. No. 62/164,929 entitled "Apparatus for Testing a Prosthesis," filed on May 21, 2015, the content of which is hereby incorporated by reference in its entirety.

TECHNICAL FIELD

This disclosure relates to an apparatus for testing a drug eluting prosthesis (e.g., a stent) that is intended to be put into a living organism such as a human being.

BACKGROUND

Drug eluting stents are used to apply treatment at the location of a stent. Depending upon its location within the body, the drug eluting stent can be exposed to forces which can affect the rate of delivery of the treatment.

SUMMARY

In accordance with embodiments of the present disclosure, an apparatus for testing a prosthesis is disclosed. The apparatus includes a first conduit frame disposed to be coupled to a first end of a conduit. The conduit is able to receive a drug eluting prosthesis. The apparatus also includes a second conduit frame disposed to be coupled to a second end of the conduit opposite the first end. The apparatus also includes a movable shaft disposed to cause relative motion between the first conduit frame and the second conduit frame. As a result of the relative motion, the drug eluting prosthesis is exposed to a tensile or compressive force. The apparatus also includes a pump for providing a flow of fluid through the conduit and the drug eluting prosthesis at least while the movable shaft is in motion. In some embodiments, a particle counter is located downstream of the conduit and disposed to receive the flow of fluid. In some embodiments, a filter is located downstream of the conduit and disposed to receive the flow of fluid. In some embodiments, the conduit is coupled to the first conduit frame using a first conduit mount including at least one tensioning element that allows the conduit to be exposed to a pre-set amount of tension or compression prior to receiving the drug eluting prosthesis. In some embodiments, a plurality of conduits are each coupled to the first conduit frame at a first end and the second conduit frame at a second end, and each conduit is disposed to receive a drug eluting prosthesis. In some embodiments, a plurality of flow lines are used to direct a separate fluid flow from each of the plurality of conduits to a particle counter or a filter. In some embodiments, the first conduit frame is a stationary conduit frame and the second conduit frame is a movable conduit frame. In some embodiments, a particle shed rate is tested prior to moving the second conduit frame relative to the first conduit frame to determine an initial particle shed rate. In some embodiments, the initial particle shed rate is compared against a particle shed rate computed while the drug eluting prosthesis is exposed to one or more of tensile and compressive forces.

Additional combinations and/or permutations of the above examples are envisioned as being within the scope of the present disclosure. It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

This description below discloses an apparatus for testing a drug eluting stent that is intended to be put into a living organism such as a human being. The stent is placed in a tube or conduit and a liquid is flowed through the conduit. Downstream of the stent a particle counter is used to determine aspects of how drug particles are shed from the stent (e.g. the particle shed rate from the stent). A filter may also be placed downstream of the stent to capture drug particles shed from the stent. While liquid is flowed through the stent, the stent is placed in tension and/or compression by stretching and/or relaxing the conduit.

Drug eluting stents and other devices that are placed within a human body or an animal can be exposed to various forces depending on their location within the body. For example, an individual's heartbeat may expose a prosthesis to various compressive or tensile forces. Thus, in order to accurately test a prosthesis or other device, it is desirable to expose the device to various forces that imitate those within the body. Such testing can provide more accurate data relating to how a device would perform once implanted within the body. Examples of other devices that could benefit from the techniques described herein include bioadsorbable stents, coated stents, or devices with other non-drug coatings.

The devices, systems, and methods disclosed herein facilitate testing of a prosthesis while exposing the prosthesis to various external forces. For example, a drug eluting prosthesis can be tested in order to determine its particle shed rate while being exposed to varying degrees of tensile and compressive forces. Such testing can help determine whether the particle shed rate varies depending on the forces exerted on the prosthesis. In other embodiments, a prosthesis can be tested to determine the effect of various forces on its possibility of failure. In still other embodiments, the effects of various bending and/or torsional forces on a prosthesis or device can be tested.

In some embodiments, numerous prostheses or devices can be tested at the same time. In one such embodiment, a number of conduits can be used to test the particle shed rate of a number of drug eluting stents, and each conduit can be associated with its own return flow tube in order to test the particle shed rate of each individual stent.

Figure 1:
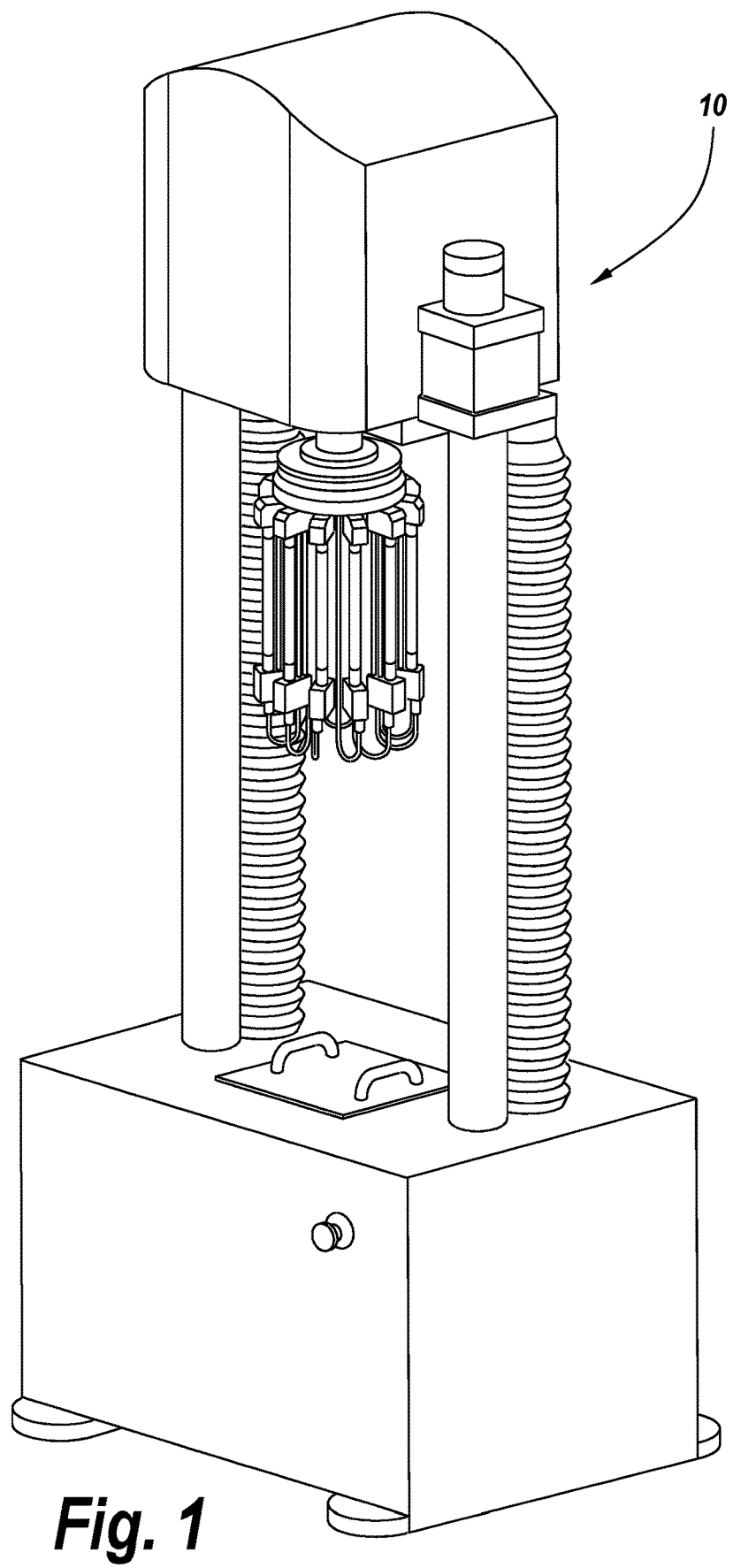
FIG. 1 shows a perspective view of an apparatus for testing a drug eluting prosthesis, according to an embodiment of the present disclosure.

FIG. 1 discloses a first portion 10 of an apparatus for testing a drug eluting stent. In this example, the apparatus is a modified ElectroForce® 3510 test instrument that is available for sale from the ElectroForce Systems Group of TA Instruments. The apparatus can also be a modified 3200 or 3330 test instrument that are also available for sale from ElectroForce. Further information on these three test instruments can be found at: tainstruments.com/wp-content/uploads/ElectroForce_Test_Instruments.pdf (and is incorporated by reference).

A second portion of the testing apparatus is the ElectroForce® 9210 system (not shown) that is available for sale from the ElectroForce. Further information on the 9210 system can be found at: tainstruments.com/wp-content/uploads/brochure_9210_031511_low.pdf (and is incorporated by reference). The 9210 system is also described in U.S. Pat. No. 8,444,935 (the '935 patent) which issued on May 21, 2013 and which is incorporated herein in its entirely by reference thereto. The 9210 system provides a source of liquid flow through the apparatus via one or more pumps.

Figure 2:
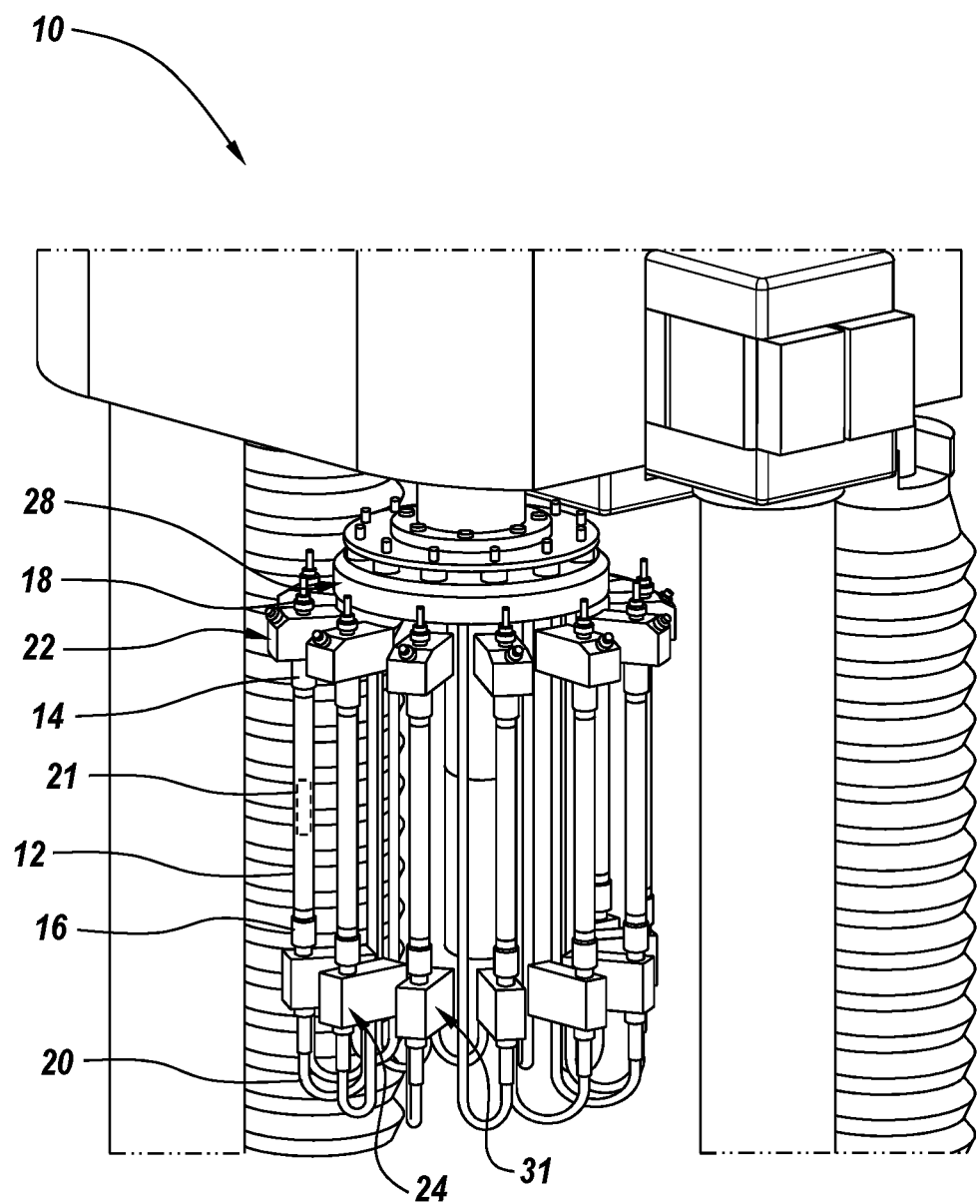
FIG. 2 shows a zoomed in perspective view of a portion of the apparatus of FIG. 1, according to an embodiment of the present disclosure.

Turning to FIG. 2, the portion 10 of the apparatus includes a series of tubes or conduits 12 which each contain a drug eluting stent e.g. prosthesis 21 (an exemplary stent is shown within one of the conduits in dashed-line format to illustrate its approximate location) approximately in the center of the conduit. In this particular embodiment, the apparatus includes twelve conduits 12, each configured to receive a drug eluting stent. The conduits 12 can be made of a flexible material such as clear silicone or latex, and can have an inside diameter that is smaller than the outside diameter of the stent. Each conduit 12 is secured at an upper end to an upper conduit mount 22 using an upper conduit fitting 14. Each conduit 12 is secured at a lower end to a lower conduit mount 24 using a lower conduit fitting 16. In this embodiment, twelve upper conduit mounts 22 are mounted onto a first conduit frame 28, and twelve lower conduit mounts 24 are mounted onto a second conduit frame 31. Thus, each conduit 12 is coupled to the first conduit frame and the second conduit frame.

A supply tube (not shown) is connected to a supply fitting 18 and supplies a flow of liquid through the conduit 12 and contained stent. The various fittings 14, 16, and 18 can be, for example, barbed fittings. The liquid flow is provided by the 9210 system and may or may not include a pulsatile component to the flow. An evacuation or return flow tube 20 allows liquid to exit the conduit 12 and return to the 9210 system where a particle counter can measure an aspect of the drug particles shed from the stent (e.g. the particle shed rate). In place of or in addition to the particle counter, a filter may be used to capture drug particles shed from the stent.

Figure 3:
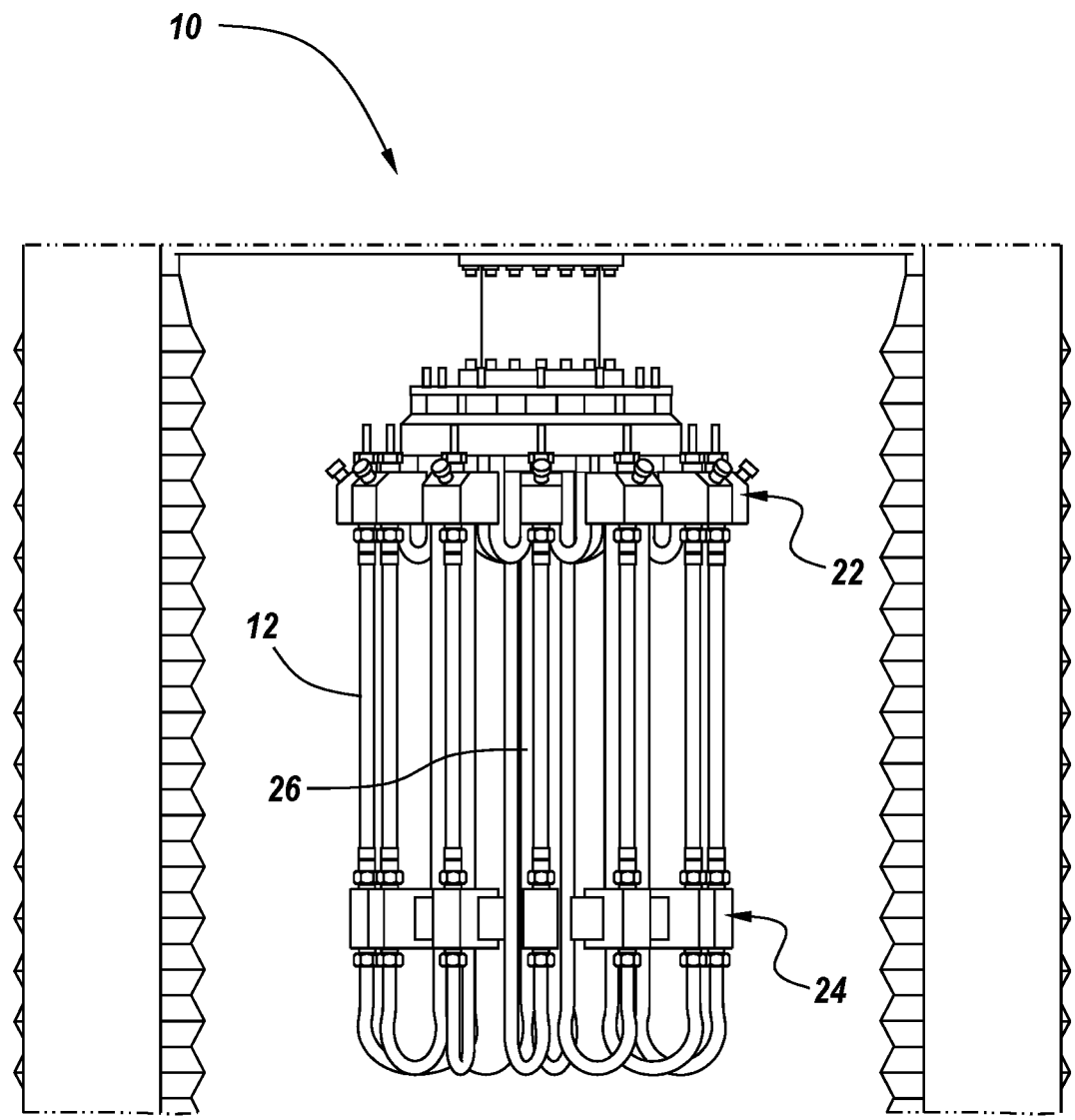
FIG. 3 shows a zoomed in front view of a portion of the apparatus of FIG. 1, according to an embodiment of the present disclosure.

Referring to FIG. 3, the portion 10 of the apparatus has a shaft 26 extending from the top middle location and operatively coupled to the first conduit frame 28 and the second conduit frame 31. The shaft 26 can be driven up and down (back and forth) by a linear electromagnet motor (not visible) located above the shaft. This motion causes the lower conduit mounts 24 to move up and down with the shaft 26, while the upper conduit mounts 22 remain substantially stationary. As a result, the conduits 12 and the respective stents inside the conduits are put in tension when the shaft 26 moves down. When the shaft 26 moves back up, the tension decreases in the conduits 12 and stents. The shaft 26 is moved up and down while liquid is flowing through the conduits 12.

In another example, a conduit 12 is stretched to put the conduit in tension prior to a stent being inserted into the conduit. The stent is then inserted into the conduit 12 while the conduit is stretched. When the tension in the conduit is released and the conduit relaxes, the stent inside the conduit is put into compression. Now the conduit 12 is connected to the barbed fittings 14 and 16. If the shaft 26 is then moved up and down by a small amount (smaller than the amount the conduit was stretched prior to inserting the stent), the stent inside the conduit will be exposed to a varying compressive force. If the shaft 26 is then moved up and down by a large amount (larger than the amount the conduit was stretched prior to inserting the stent), the stent inside the conduit will be exposed to a varying compressive and tensile force. As such, the stent inside the conduit can be exposed to one or more of tensile forces and compressive forces while liquid is being flowed through the stent.

Figure 4:
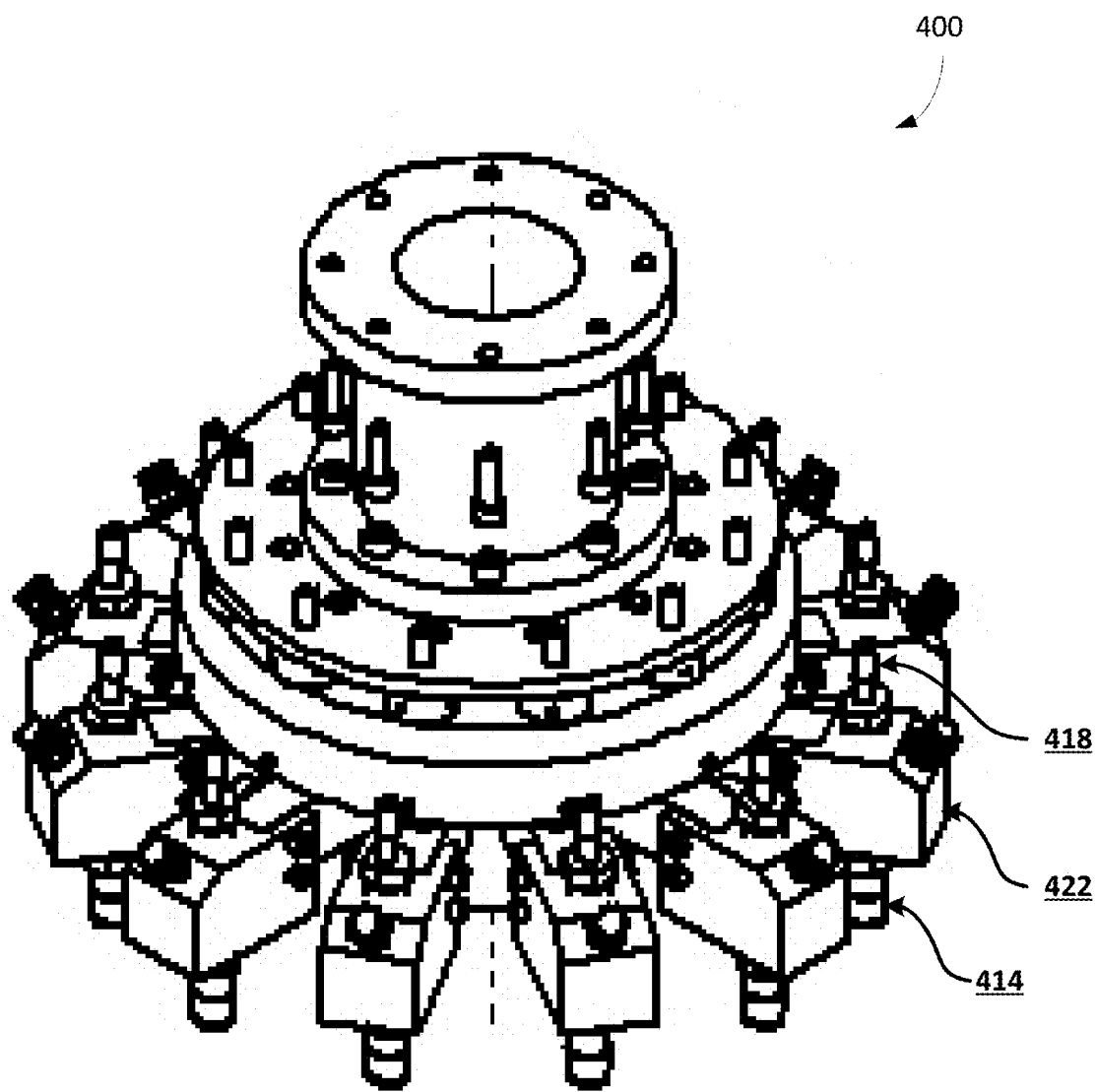
FIG. 4 shows a perspective view of a stationary portion of the apparatus of FIG. 1, according to an embodiment of the present disclosure.

FIG. 4 shows a perspective view of a stationary portion 400 of an apparatus for testing a drug eluting stent, according to an embodiment of the present disclosure. In this particular example, the stationary portion 400 includes an array of stationary conduit mounts 422. As will be appreciated, various embodiments may include more or fewer stationary conduit mounts 422. In some embodiments, a conduit, as described above, can be coupled to each stationary conduit mount 422 using a stationary conduit fitting 414, and a supply tube (not shown) can be coupled to each stationary conduit mount 422 using a supply fitting 418. The supply tube is coupled in fluid communication with the conduit via the fittings 414 and 418 and the stationary conduit mount 422 such that a fluid can pass from the supply tube and through the conduit.

Figure 5:
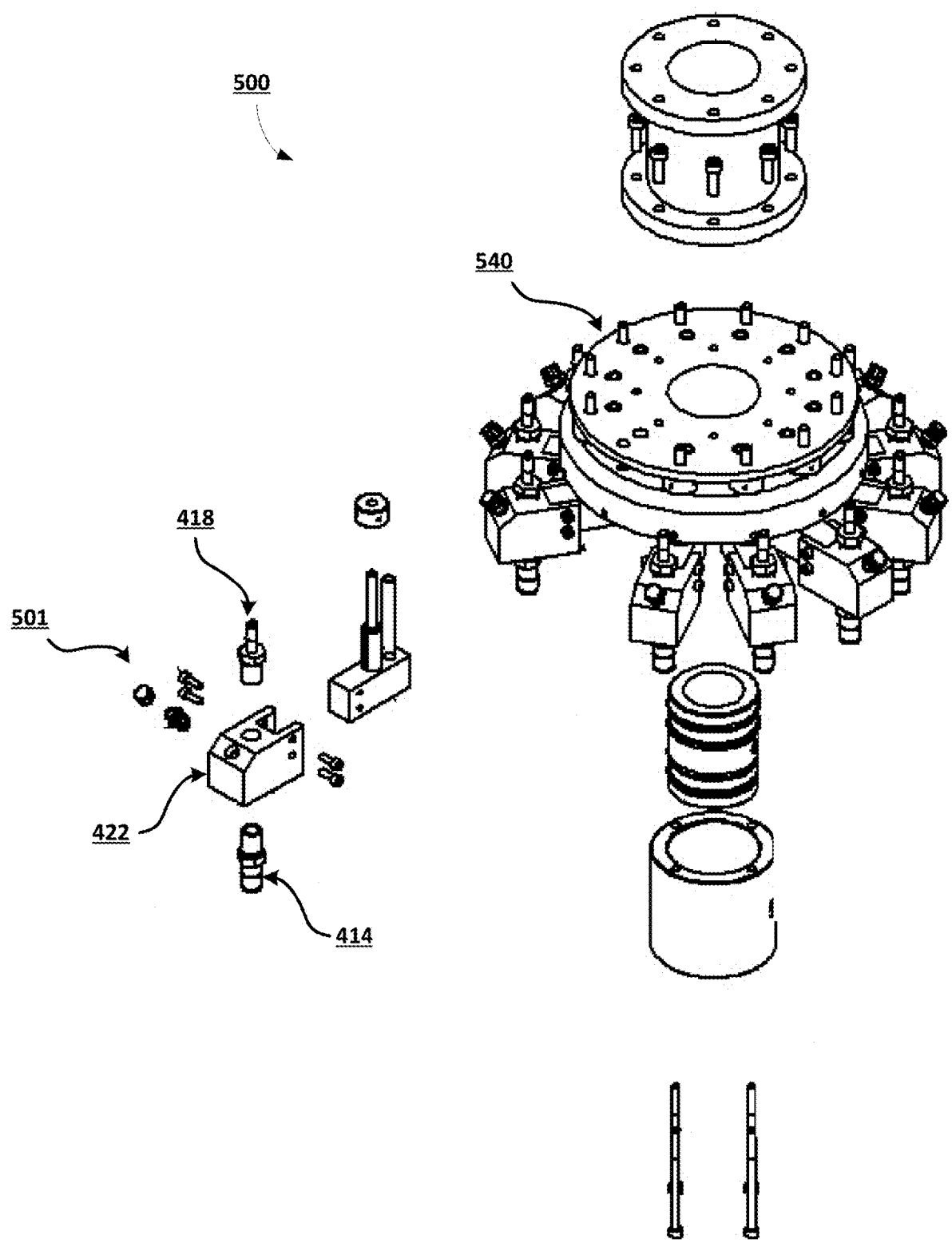
FIG. 5 shows an exploded view of the stationary portion of FIG. 4, according to an embodiment of the present disclosure.

FIG. 5 shows an exploded view 500 of the stationary portion of FIG. 4, according to an embodiment of the present disclosure. As can be seen in this example, a number of stationary conduit mounts 422 can be mounted onto a stationary conduit frame 540. A supply fitting 418 can be a hollow fitting that fits within a bore of the stationary conduit mount 422. The stationary conduit fitting 414 can also be a hollow fitting that fits within the bore of the stationary conduit mount 422. In some embodiments, the stationary portion can include one or more tensioning elements 501 that allow pre-tension of each conduit that is coupled to the stationary conduit fittings 414.

Figure 6:
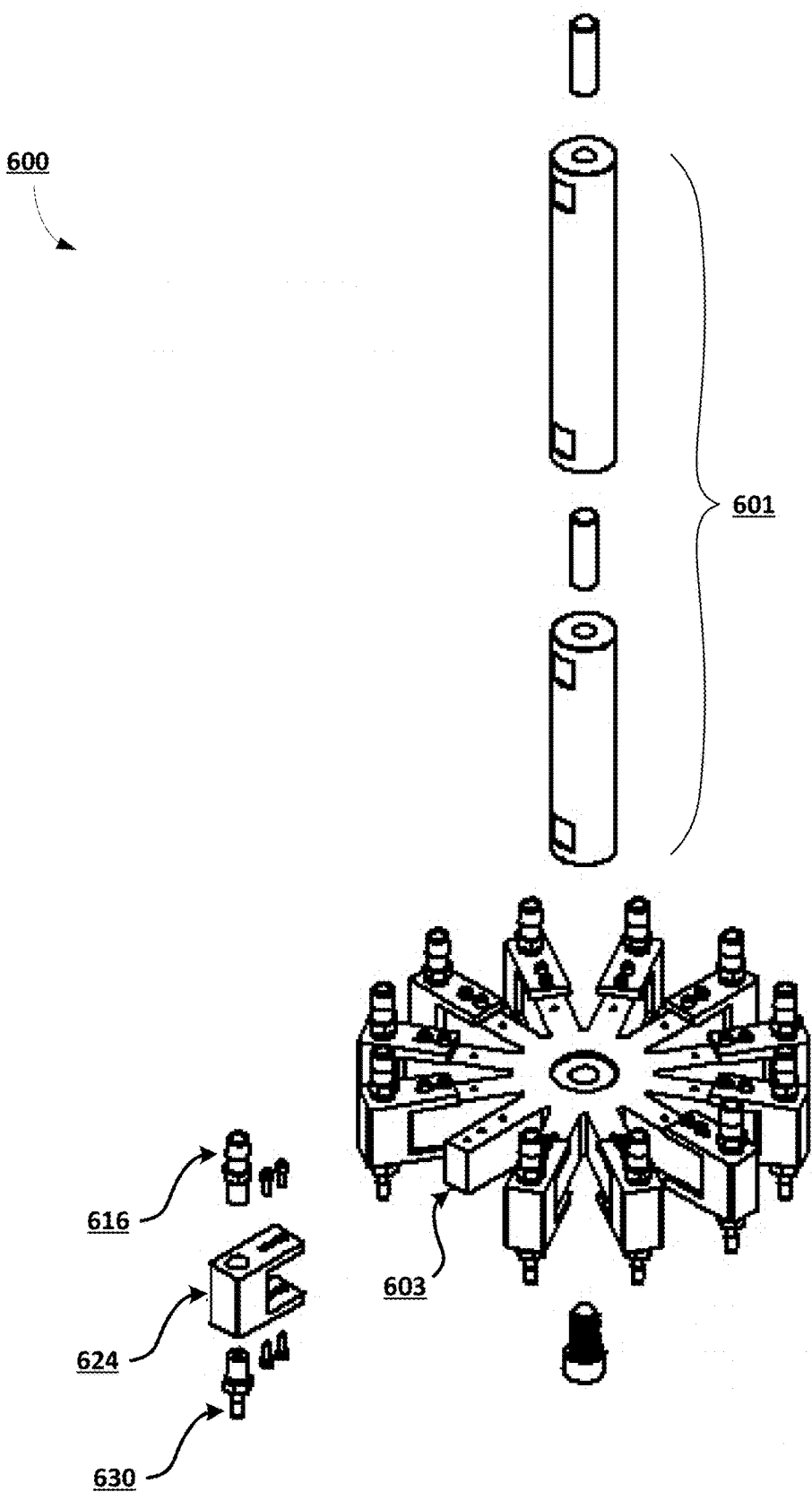
FIG. 6 shows an exploded view of a movable portion of the apparatus of FIG. 1, according to an embodiment of the present disclosure.

FIG. 6 shows an exploded view 600 of a movable portion of an apparatus for testing a drug eluting stent, according to an embodiment of the present disclosure. The movable portion includes a movable conduit frame 603, onto which a number of movable conduit mounts 624 can be mounted.

A substantially hollow movable conduit fitting 616 can couple to a conduit (not shown) and fit within a bore of the movable conduit mount 624. A substantially hollow return flow fitting 630 can couple to a return flow tube (not shown) and also fit within the bore of the movable conduit mount 624 in order to provide fluid communication between the conduit and the return flow tube. In some embodiments, a separate return flow tube can direct fluid passing from each conduit to a particle counter or filter. Separate return flow tubes can be used for each conduit in order to independently test each prosthesis within the conduits. As discussed above, the movable portion can move relative to the stationary portion in order to exert compressive and tensile forces on a prosthesis within the conduit. In some embodiments, the movable conduit frame 603 is attached to a shaft assembly 601, which is operatively coupled to a motor that can move the movable conduit frame 603 relative to the stationary portion of the system. In exemplary embodiments, a linear electromagnetic motor causes the shaft assembly 601 to telescope up and down to move the movable conduit frame 603 relative to the stationary portion of the system. This motion can apply various compressive and tensile forces to a prosthesis located within a conduit, as described above.

Figure 7:
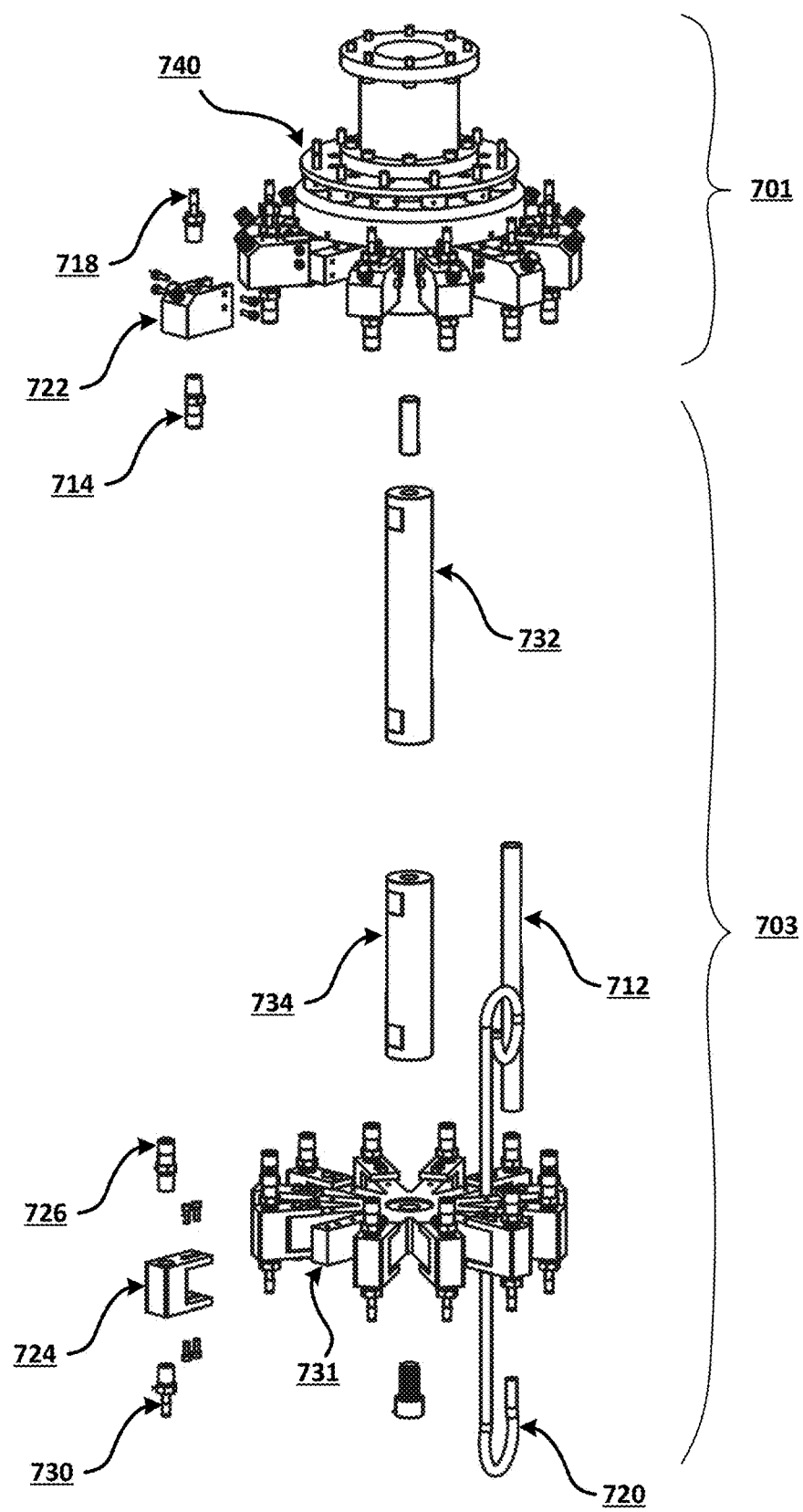
FIG. 7 shows an exploded view of the stationary portion of FIG. 4 and the movable portion of FIG. 6, according to an embodiment of the present disclosure.

FIG. 7 shows an exploded view of a stationary portion 701 and a movable portion 703 of an apparatus for testing a drug eluting stent, according to an embodiment of the present disclosure. The stationary portion 701 can include a number of stationary conduit mounts 722 mounted onto a stationary conduit frame 740, and the movable portion can include a number of movable conduit mounts 724 mounted onto a movable conduit frame 731. In this example, a conduit 712 is attached to a stationary conduit mount 722 via a stationary conduit fitting 714. The conduit 712 is also attached, at an opposite end, to a movable conduit mount 724 via a movable conduit fitting 726. A supply tube (not shown) can be coupled to the stationary conduit mount 722 via a supply fitting 718. The supply tube is coupled in fluid communication with the conduit 712 such that fluid can pass from the supply tube through the conduit 712. In some embodiments, the various components of the stationary portion 701 allow pre-tension of each conduit 712 that is coupled to a stationary conduit fitting 714.

The movable conduit mounts 724 can be mounted onto a movable conduit frame 731, that is in turn attached to movable shaft elements 732 and 734. The movable shaft elements 732 and 734 can be operatively coupled to a motor in order to move the movable conduit frame 731 relative to the stationary portion 701. As discussed above, a prosthesis, such as a drug eluting stent, can be placed within the conduit 712, and the motion of the movable conduit frame 731 relative to the stationary portion 701 can apply various compressive and tensile forces to a prosthesis located within the conduit 712. A return flow fitting 730 can be used to couple a return flow tube to a bore of the movable conduit mount 724. The movable conduit fitting 726, movable conduit mount 724, and return flow fitting 730 provide fluid communication between the conduit 712 and return flow tube 720 such that fluid passing through a prosthesis within the conduit 712 can pass through the return flow tube 720 to a particle counter or filter. In this particular embodiment, each conduit 712 is attached to a single motor (e.g. a single linear motor) via the movable conduit frame 731, but there is a separate fluid path through each conduit 712 in order to independently monitor the particle shed rate of each prosthesis positioned within the conduits 712.

Figure 8:
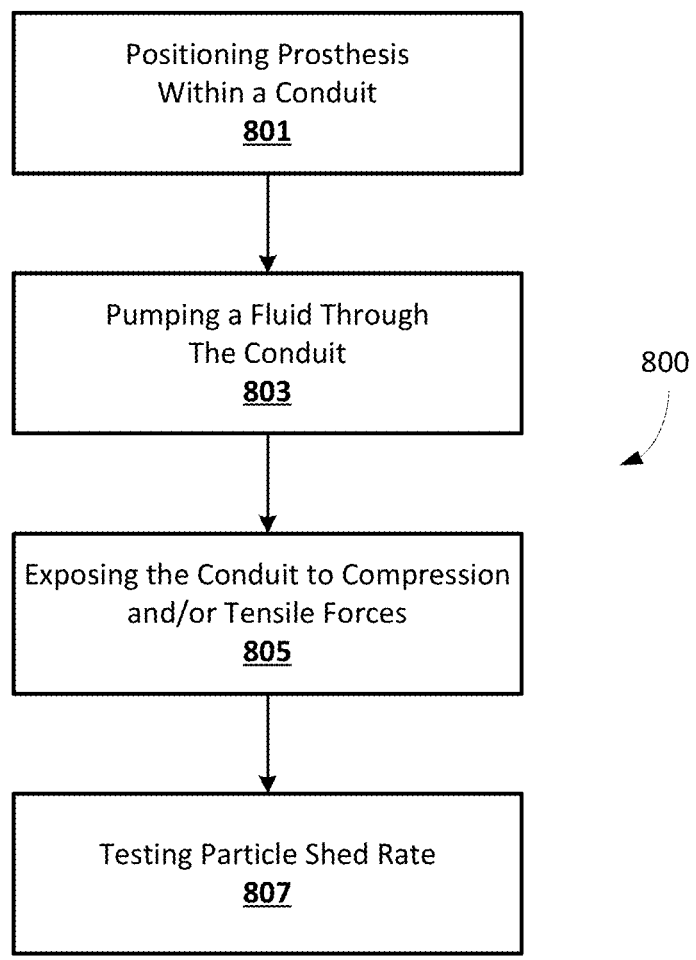
FIG. 8 is a flowchart illustrating an exemplary method of testing a prosthesis, according to an embodiment of the present disclosure.

FIG. 8 is a flowchart 800 illustrating an exemplary method of testing a prosthesis, according to an embodiment of the present disclosure. In step 801, a prosthesis, such as a drug eluting stent, is positioned within a flexible conduit. As discussed above, the conduit can be made of a flexible material, such as clear silicone or latex, and can have an inside diameter that is smaller than the outside diameter of the stent. Each conduit can be secured at one end to a stationary conduit mount, and at a second end to a movable conduit mount. The movable conduit mount can be coupled, either directly or indirectly, to a movable shaft that can move the movable conduit mount with respect to the stationary conduit mount and thus apply compressive and tensile forces to the conduit. When the conduit is exposed to compressive and tensile forces, the drug eluting stent positioned within the conduit is also exposed to compressive and tensile forces.

In step 803, a fluid is pumped through the conduit and through the drug eluting stent within the conduit. As discussed above, a fluid can be pumped to a supply tube that is in fluid communication with the conduit through the stationary conduit mount, in some embodiments. The fluid can be pumped through the drug eluting stent and be directed to a particle counter or filter via a return flow tube.

In step 805, the conduit is exposed to compressive and/or tensile forces by moving the movable conduit mount relative to the stationary conduit mount. When the conduit is exposed to the compressive or tensile forces, the drug eluting stent within the conduit is also exposed to compressive or tensile forces. In some embodiments, the conduit can be stretched or compressed at a pre-set compression or tension level before positioning a drug eluting stent within the conduit.

In step 807, the particle shed rate of the drug eluting stent is tested using a particle counter or filter located downstream of the drug eluting stent. The particle counter can be used to determine aspects of how drug particles are shed from the drug eluting stent, while a filter can capture drug particles shed from the stent.

In some embodiments, an initial particle shed rate is determined before the drug eluting stent is exposed to any compressive or tensile forces. After the drug eluting stent is exposed to a compressive or tensile force, a second particle shed rate can be determined, and the system can compare the initial particle shed rate against the second particle shed rate. Thus, data can be gathered relating to the impact various forces have on the particle shed rate of a drug eluting stent.

A number of implementations have been described. Nevertheless, it will be understood that additional modifications may be made without departing from the scope of the inventive concepts described herein, and, accordingly, other embodiments are within the scope of the following claims.

What is claimed is:

1. An apparatus for testing a prosthesis, comprising:
   a first conduit frame disposed to be coupled to a first end of a conduit, wherein the conduit is disposed to receive a prosthesis;
   a second conduit frame disposed to be coupled to a second end of the conduit opposite the first end;
   a movable shaft disposed to cause relative motion between the first conduit frame and the second conduit frame, the prosthesis thereby being exposed to a tensile or a compressive force as a result of the relative motion; and
   a pump fluidly connected to the conduit to provide a flow of fluid through the conduit and the prosthesis at least while the movable shaft is in motion.

2. The apparatus of claim 1, wherein the prosthesis is a drug eluting prosthesis.

3. The apparatus of claim 1, further comprising a particle counter located downstream of the conduit and disposed to receive the flow of fluid.

4. The apparatus of claim 1, further comprising a filter located downstream of the conduit and disposed to receive the flow of fluid.

5. The apparatus of claim 1, wherein the conduit is coupled to the first conduit frame using a first conduit mount including at least one tensioning element that allows the conduit to be exposed to a pre-set amount of tension or compression prior to receiving the prosthesis.

6. The apparatus of claim 1, further comprising a plurality of conduits, wherein each conduit is coupled to the first conduit frame at a first end and the second conduit frame at a second end, and wherein each conduit is disposed to receive a prosthesis.

7. The apparatus of claim 6, further comprising a plurality of flow lines, each flow line disposed to direct a separate fluid flow from each of the plurality of conduits to one of a particle counter or a filter.

8. The apparatus of claim 1, wherein the first conduit frame is a stationary conduit frame and the second conduit frame is a movable conduit frame.

\* \* \* \* \*